United States Patent

Bailey et al.

[11] Patent Number: 6,028,315
[45] Date of Patent: *Feb. 22, 2000

[54] CLEANING APPARATUS

[75] Inventors: William Bailey, Great Rissington; Richard Little, Freemantle, both of United Kingdom

[73] Assignee: The Body Shop International PLC, United Kingdom

[*] Notice: This patent issued on a continued prosecution application filed under 37 CFR 1.53(d), and is subject to the twenty year patent term provisions of 35 U.S.C. 154(a)(2).

[21] Appl. No.: 08/817,271
[22] PCT Filed: Sep. 26, 1995
[86] PCT No.: PCT/GB95/02278
   § 371 Date: Nov. 20, 1997
   § 102(e) Date: Nov. 20, 1997
[87] PCT Pub. No.: WO96/09842
   PCT Pub. Date: Apr. 4, 1996

[30] Foreign Application Priority Data

Sep. 27, 1994 [GB] United Kingdom ............ 9419547
Jan. 17, 1995 [GB] United Kingdom ............ 9500866
May 1, 1995 [GB] United Kingdom ............ 9508824

[51] Int. Cl.$^7$ .................. G01N 23/00; G01N 21/00
[52] U.S. Cl. ....................... 250/455.11; 250/454.11
[58] Field of Search ................... 250/454.11, 455.11

[56] References Cited

U.S. PATENT DOCUMENTS

| | | | |
|---|---|---|---|
| 2,194,463 | 3/1940 | Powley | 250/5 |
| 4,786,812 | 11/1988 | Humphreys | 250/455.11 |
| 4,981,651 | 1/1991 | Horng | 250/455.11 |
| 5,166,528 | 11/1992 | Le Vay | 250/455.11 |
| 5,614,151 | 3/1997 | Le Vay et al. | 250/455.11 |

FOREIGN PATENT DOCUMENTS 0277505  1/1987  European Pat. Off. .

*Primary Examiner*—Bruce C. Anderson
*Attorney, Agent, or Firm*—Shook, Hardy & Bacon, L.L.P.

[57] ABSTRACT

Sterilizing apparatus for sterilizing a container comprises an elongate light bulb (4, 18, 111) adapted to emit ultra violet light when energized by microwaves, and a shield (16, 110) substantially surrounding said bulb (4, 18, 111) and being adapted to support a container (6) so that said bulb is located within the container. The shield (16, 110) is transparent to microwaves.

19 Claims, 8 Drawing Sheets

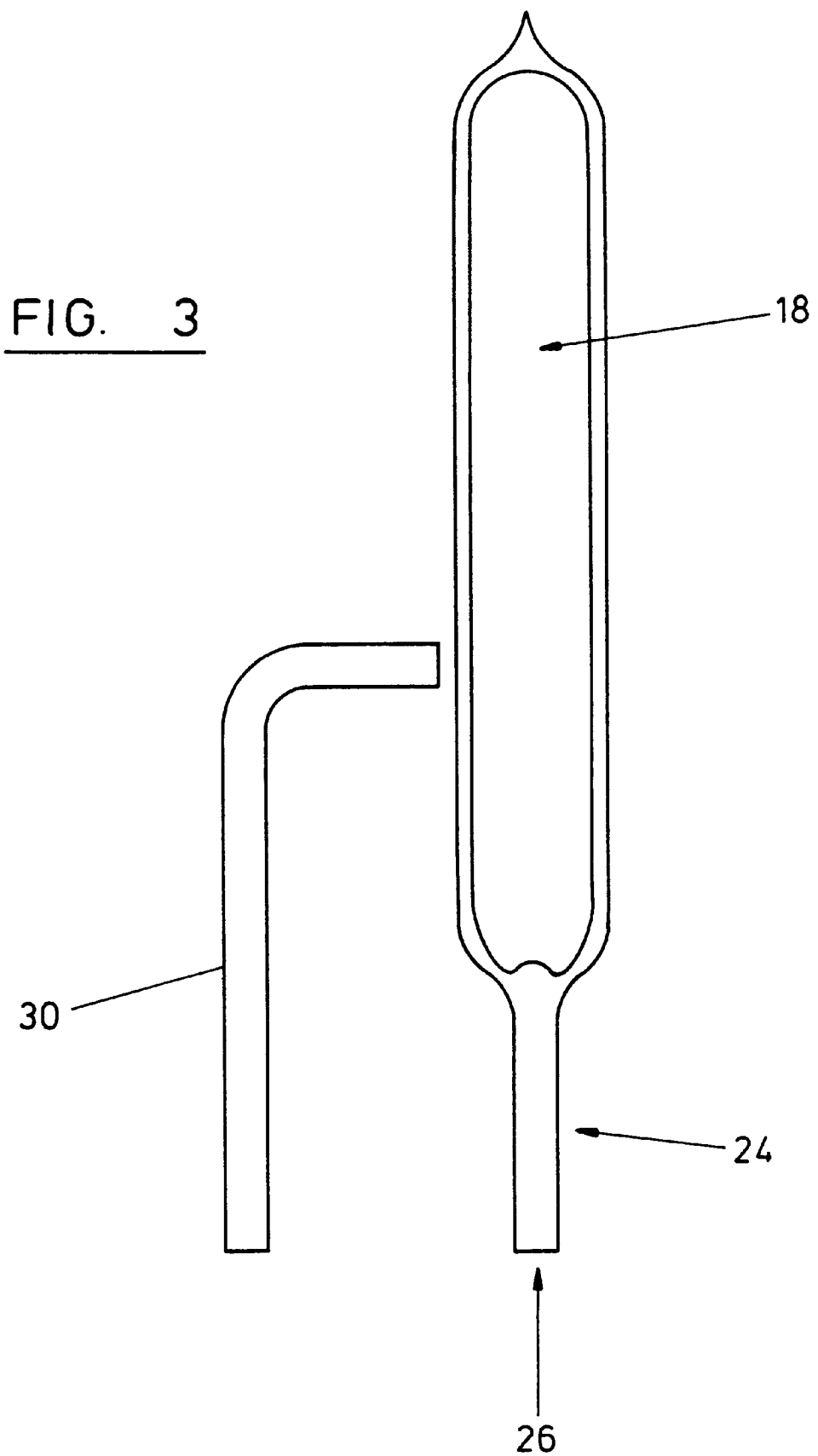

CLEANING APPARATUS

This invention relates to cleaning apparatus and, particularly but not exclusively, to apparatus adapted to dry and sterilise containers used to contain liquids such as cosmetics, toilet preparations and the like.

In recent years, environmental issues have become of increasing interest and one particular concern is the question of waste disposal. One particular problem is the amount of packaging material used in products, some of which is immediately discarded once the product is purchased, whilst the product container is disposed of once the product is used. The products themselves are frequently supplied in so-called disposable containers such as bottles formed of synthetic plastics material or glass. This packaging is traditionally disposed of by dumping or incineration. These methods have a number of disadvantages, namely the loss of material, the energy use of production and the problems associated with finding sufficient sites to accommodate the rubbish and the inherent pollution problems when a wide variety of materials is dumped in one site. A further problem is that much of the dumped material is non-biodegradable and therefore remains in the ground as a potential pollutant for many hundreds of years.

It has been proposed to re-use containers by offering a refill service in which the containers are re-used a number of times. In order to reduce the problems of cost and transport in transporting empty containers back to a central factory or warehouse, there are advantages in refilling containers at local centres such as retail shops. One problem associated with such local refilling is the problem of ensuring that the containers are clean and sterile so that the new product is not contaminated as soon as it is placed in the container. Known methods consist of the purchaser or shop simply washing the containers out using the normal water supply but this method does not ensure that the container is satisfactorily clean and sterile and also raises further environmental problems.

It has been found that one of the reasons why customers do not use the existing refill systems as much as they might is the length of time it takes to clean and dry the containers and actually carry out the refilling operation. It is one object of the present invention to develop apparatus to speed up this process so that the time the refilling service takes is sufficiently short to encourage the customer to use the service.

The present invention seeks to provide apparatus which could be used in a small shop, or even in domestic premises, to ensure that bottles are dry and sterile before re-use.

According to the present invention there is provided sterilising apparatus for sterilising a container, the apparatus comprising an elongate member adapted to emit ultra violet light having sterilising properties when energised, and a shield substantially surrounding said member and being adapted to shield said elongate member from physical damage, wherein, in order to sterilise the interior of a container, the elongate member is located at least partially within the container and energised.

A preferred form of the apparatus includes a microwave generator, adapted to generate microwaves, the elongate member being adapted to emit ultra violet light when irradiated by operation of said microwave generator, the shield being transparent to microwaves.

In one embodiment, the elongate member and the surrounding shield are disposed in an upstanding manner in a chamber. In a preferred embodiment, the elongate member and the surrounding shield are mounted on a side wall of the chamber which is preferably opposite a door of the chamber.

In another embodiment, the chamber incorporates a hinged door, the elongate member and the shield being mounted on the inner surface of said door so that when the door is opened the elongate member and shield are clearly exposed to facilitate the placement of a container over the shield. Operation of the sterilising apparatus may be triggered by closing the door to thereby close a contact which then initiates irradiation of the ultra violet light source. Control means may be provided to adjust the length of time that the elongate member is irradiated.

In a development of the invention, the shield comprises a closed tube formed of a plastics material which is substantially transparent to ultra violet light and microwaves. Preferably, the apparatus includes means to supply air or an inert gas such as nitrogen to the interior of the shield to cool the elongate member when it is emitting ultra violet light. The tube preferably incorporates orifices towards its upper end so that the air leaves the tube and enters the interior of the container being sterilised. In this way, the air warmed by the ultra violet light, assists in removing particles of foreign matter and moisture from the interior of the container.

In an alternative form, the tube comprises an open framework or lattice work. In such an arrangement, the material of the shield may not necessarily be transparent to microwaves, providing the openings in the shield are sufficient to allow the microwaves to penetrate to irradiate the elongate member. It is also conceivable that the shield may incorporate, or consist of, the waveguides of the magnetron. Since the tube, when sterilising a container, is substantially entirely within the container, it will be possible for this form of the apparatus to sterilise containers which are not transparent to microwaves.

The chamber containing the air tube may have an outlet vent incorporating a mist eliminator, which may be in the form of a wire mesh, to trap particles of water and vapour contained in the air being vented from the container. The apparatus preferably also includes a drip tray for moisture driven out of the container and/or the mist eliminator.

The device may include a bulb support or stand for permitting the device to be free-standing in a microwave oven so that the article in the form of a container with an open end may be upturned and placed over the bulb prior to turning the oven on. Alternatively the device may comprise means for suspending the device from the neck of the article so that it hangs down within the article or means for gripping the article to support it in a generally horizontal position around the bulb.

Preferred embodiments of the invention will now be described by way of example with reference to the accompanying drawings in which:

FIG. 3 is an enlarged sectional view of an UV bulb for use in the apparatus of FIG. 2;

Figure 1:
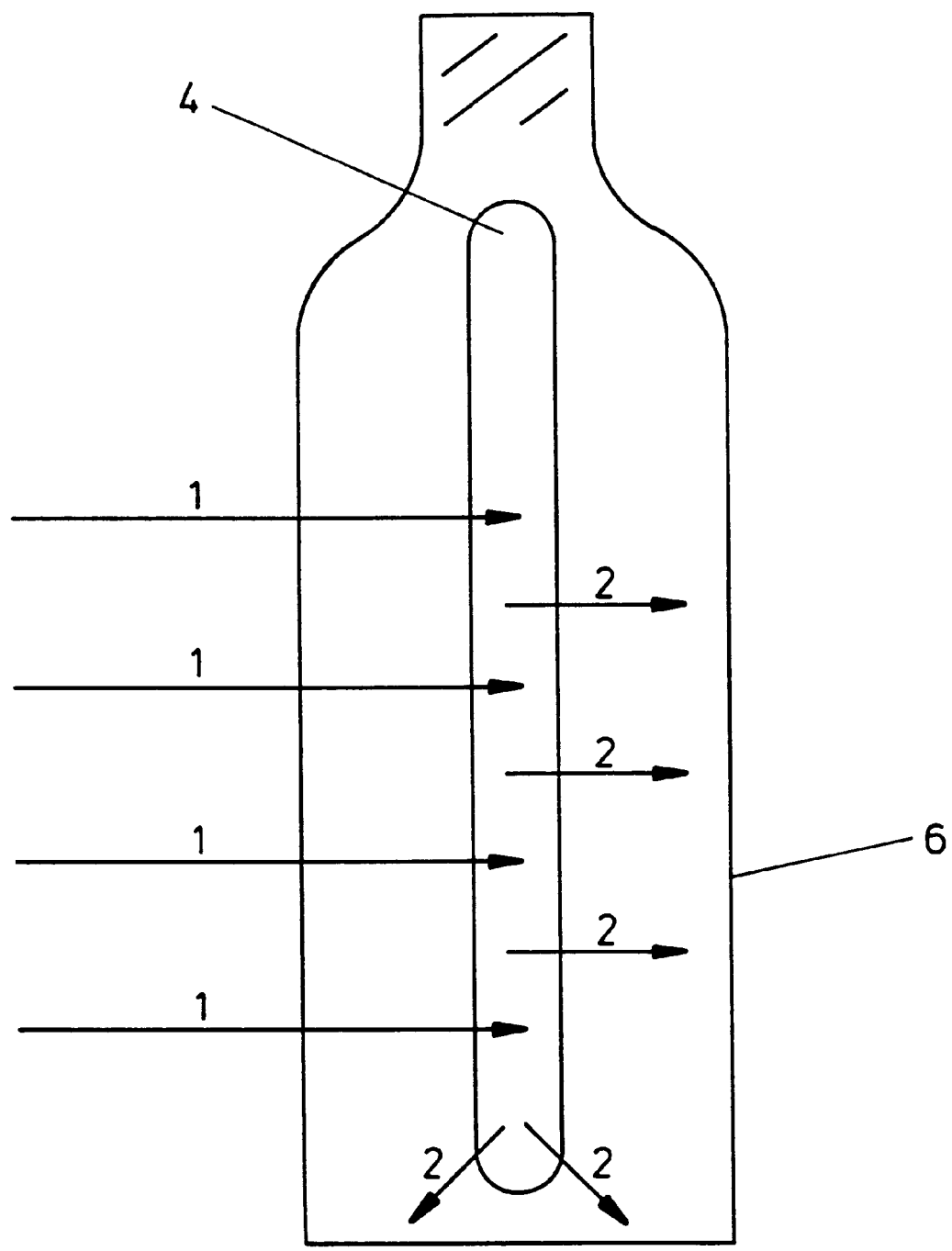
FIG. 1 is a sectional view of an UV bulb inside a hollow article for sterilising the article in accordance with the invention.

With reference to FIG. 1 illustrating the principle of the invention, a microwave energisable UV bulb 4 is suspended inside an article 6 to be sterilised (in this case a bottle). The bulb 4 is energised by incident microwave energy (indicated by arrows 1) and, as a result, radiates UV energy (indicated by arrows 2) outwardly to sterilise the interior surface of the article 6. It has been found that the preferred range of wavelengths of UV energy is from 200 nm to 280 nm, the most effective range being from 200 nm to 260 nm. A bulb such as Model No. F300 H+ produced by Fusion Systems, Inc. of Washington, U.S.A. has been successfully used in trials.

The bulb 4 and article 6 may be one of a plurality of such bulbs and articles progressing along a production line, the insertion and removal of the bulb or bulbs being automated. Advantageously, the production line is equipped with shutters to permit the article or articles 6 to enter and exit an electrically conducting enclosure before the microwave source (not shown) is switched on. This ensures that the microwave energy is contained in the area of the articles 6 both to maximise safety and efficiency.

In an alternative configuration, the article is suspended in an upturned position over an upstanding UV bulb.

In a preferred sterilisation device in accordance with the invention, the bulb 4 is generally cylindrical in shape and is approximately the same length as the height of the article to be sterilised. The bulb 4 is provided with a non-metallic stand which allows the bulb 4 to be stood generally vertically in a domestic microwave oven. In use, the article 6 is placed over the free-standing bulb 4 and the oven switched on. This provides a convenient means of domestic sterilisation.

In a further embodiment, the bulb 4 is adapted for insertion in a baby's milk bottle and the bulb 4 is of a suitable power to provide effective sterilisation when used with a domestic microwave oven. The bulb 4 may either be free-standing as described above or may be secured to a support so that it may be hung from the neck of the bottle.

In a further embodiment, the bulb 4 is suspended inside the article 6 using magnetic or fluid pressure means. Using such suspension means is particularly advantageous where the article 6 is a continuous material such as a continuous length of tubing. By using a non-contact means of suspension, the bulb 4 may be held substantially stationary in the microwave energy field and the article 6 may be passed over the bulb 4 at a rate calculated to provide sufficient sterilisation.

Figure 2:
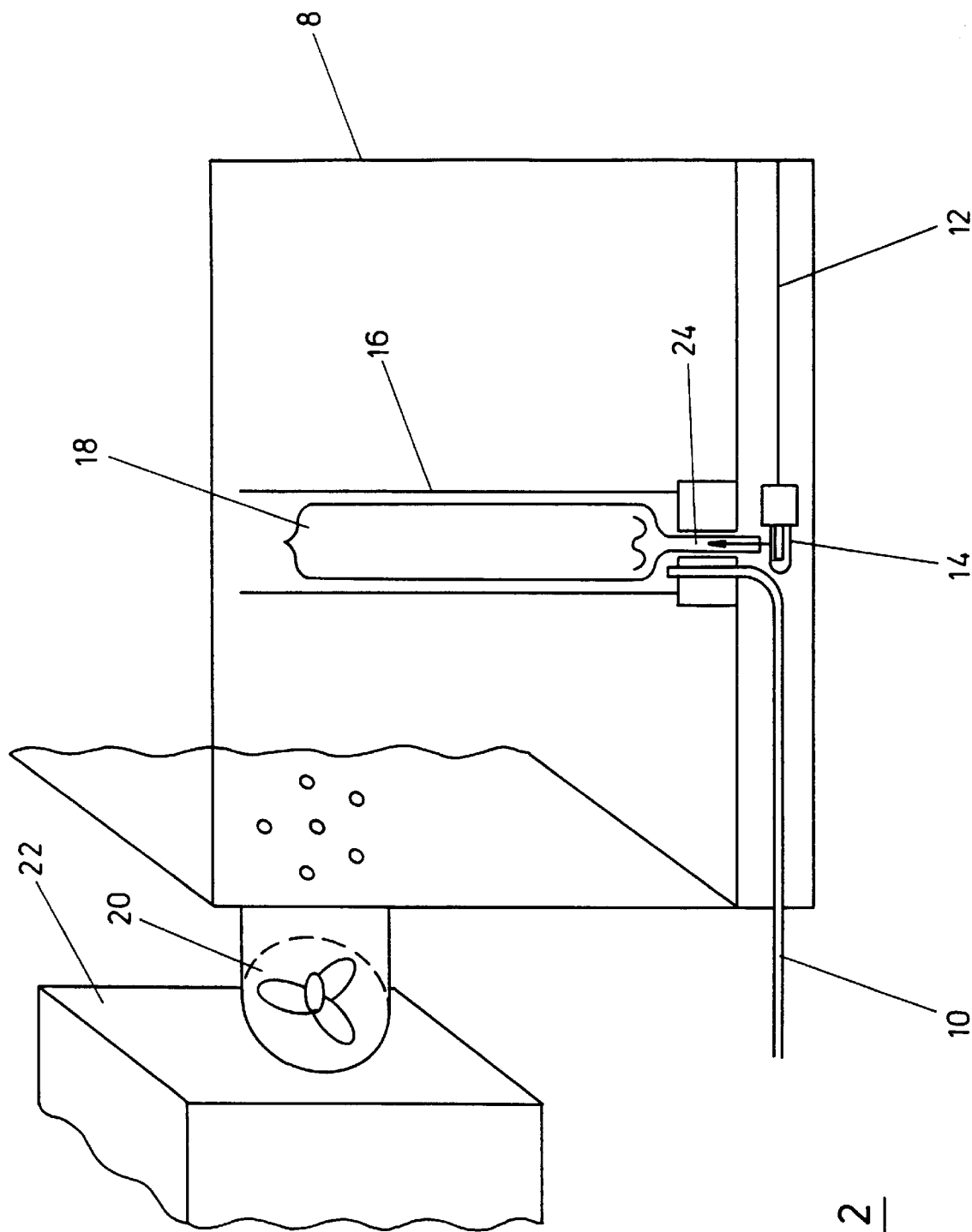
FIG. 2 is a diagrammatic and partly sectional view of a sterilisation device in accordance with the invention.

With reference to FIG. 2, a sterilisation device in accordance with the invention has a microwave enclosure 8 (only a fragment of which is shown) which is supplied with cooling air via pipe 10 and electrical power via cable 12 for activating a trigger bulb 14 (typically an arc or filament UV bulb) located in a lower part of the enclosure 8.

The jacket 16, air inlet and bulb 18 are arranged so that air is caused to flow into the jacket 16 at one end, past the bulb 18 and out of the jacket 16 at its other end and into the enclosure 8. Additional air inlets may be provided as necessary. The cooling jacket 16 is substantially transparent both to microwave energy and to UV energy and may be made of quartz. Thus microwave energy is able to energise the bulb 18 and the resulting UV energy radiated by the bulb 18 is able to reach an article to be sterilised surrounding the jacket 16. The article is not shown in FIG. 2.

Air is extracted from the enclosure 8 by fan 20 through ozone filter 22 and exhausted to the atmosphere.

Microwave energy is shown entering the enclosure 8 by arrows A. The energy is fed into the enclosure 8 from a magnetron via a suitable waveguide and launcher in a manner known in the art. The enclosure 8 is provided with suitable safety interlocks and is constructed such that microwave energy is unable to escape from the enclosure 8.

The enclosure is provided with means to allow the article to be sterilised to be introduced into the enclosure. The means may, for example, be a door or shutter arrangement permitting the enclosure 8 to be brought down onto an article on a conveyor belt or alternatively permitting an article to pass through the enclosure 8 on a conveyor belt.

The trigger bulb 14 is caused to radiate UV energy briefly when microwave energy is being fed into the enclosure 8 in order to trigger the bulb 18. This UV energy is fed to the bulb 18 via an elongate extension 24 of the bulb 18. As shown in FIG. 3, the extension 24 is in the form of a shaft which operates in the manner of an optical fibre by conducting energy entering a face 26 of the shaft from the bulb 14 along the shaft to the bulb 18, there to be absorbed by the bulb gas (or fill) so as to trigger the bulb 18 into its UV radiating mode. The shaft is also used for mounting the bulb 18 in the enclosure 8. Alternatively or additionally, a separate (preferably quartz) light conducting bar 30 may be provided, arranged so that its two ends are held adjacent each respective bulb.

Figure 4A:
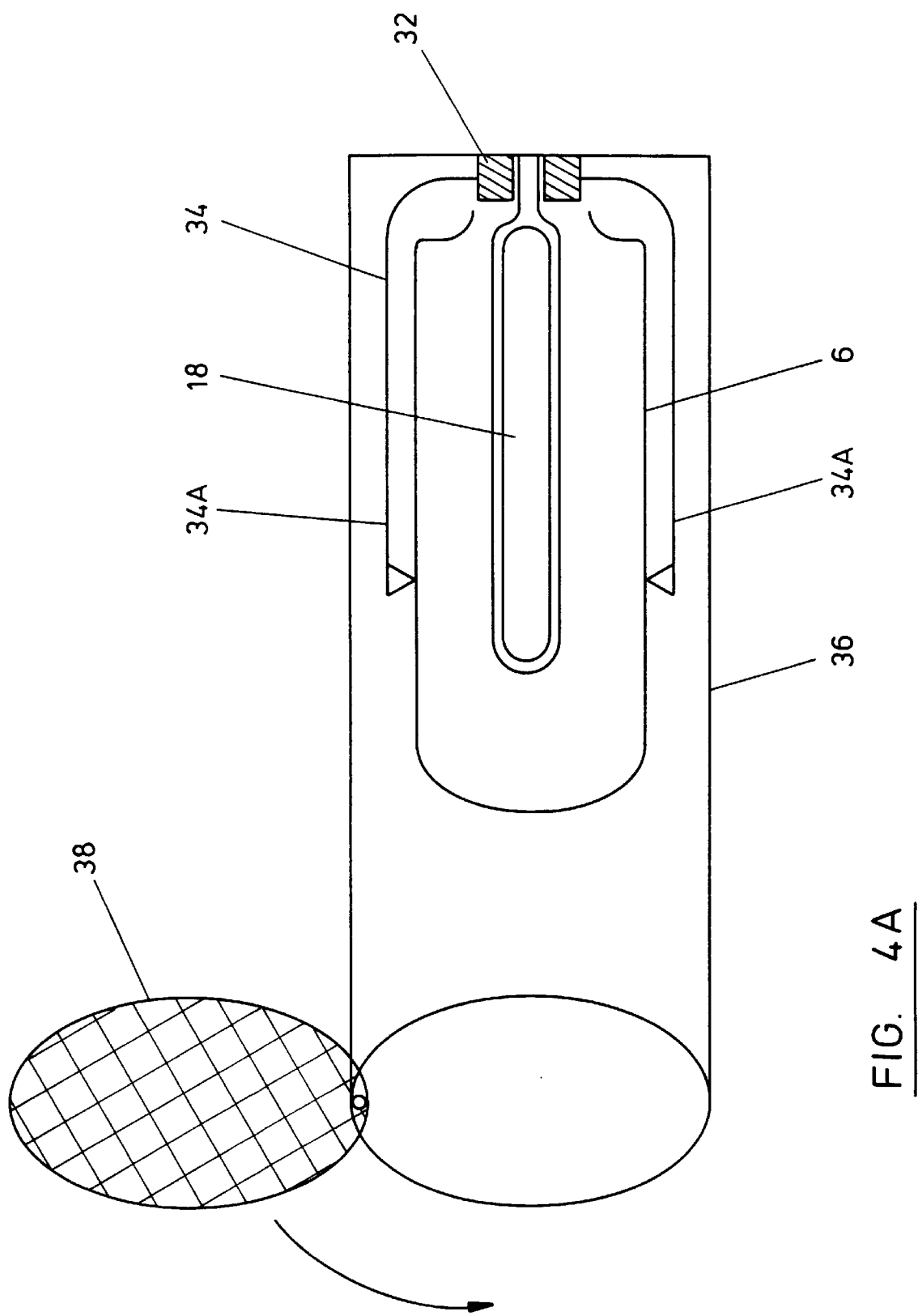
FIG. 4A is a sectional view of an alternative sterilisation device in accordance with the invention.

The embodiment shown in FIG. 4A is intended to be used in a domestic or laboratory microwave oven. With reference to the Figure, the bulb support comprises a mounting block 32 from which a resilient clip 34 extends. In this embodiment, the shaft 24 of bulb 18 is also mounted in the block 32.

The clip 34 is arranged to grip and support the article 6 which is to be sterilised. The sectional view in the Figure shows only two arms 34A of the clip 34 although it will be appreciated that a practical embodiment is likely to have three or more clips spaced equiangularly around the circumference or periphery of the article 6. Since it is advantageous for the clip 34 and block 32 to be transparent at microwave frequencies, they are typically made from a plastics material.

The block 32 is mounted at one end of a case 36. The case surrounds the article 6, bulb 18 and clips 34. It will be appreciated that it is undesirable to permit leakage of the UV energy emitted by the bulb 18 during sterilisation. A domestic or laboratory microwave oven usually has a glass window which allows at least some UV energy to pass through. To prevent this, the case 36 may be arranged to prevent closing of the oven door until it is itself closed. By making the case UV opaque, the UV energy is then prevented from leaking during sterilisation. One way of preventing closing of the door is to arrange for the case 36 to be larger than the internal dimensions of a typical microwave oven until the case 36 is closed. The case 36 is therefore fitted with a hinged lid 38 which when open, projects to one side of the case 36. The lid 38 projects sufficiently to make the case 36 too large to fit inside a typical domestic or laboratory microwave oven.

Figure 4B:
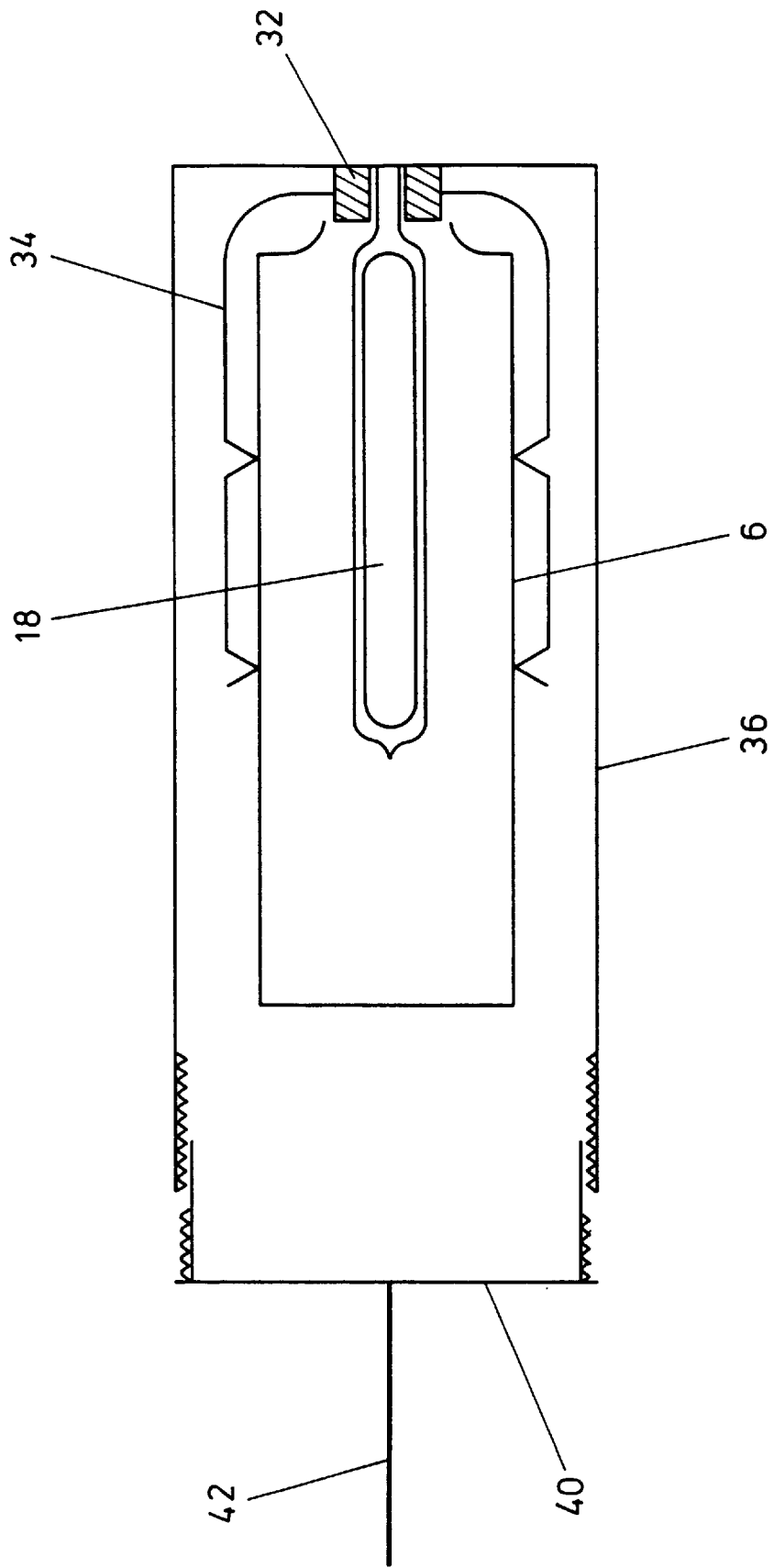
FIG. 4B is a sectional view of a further alternative sterilisation device in accordance with the invention.

FIG. 4B shows an alternative construction for the case 36 of FIG. 4A. In this alternative construction, the case 36 has a screw-fitted cap 40 which has an elongate member 42 extending axially of the case 36 and which causes the case and cap 40 in combination to be too long to fit into a typical domestic or laboratory microwave oven until the cap 40 is screwed home.

If the microwave oven does not permit leakage of UV energy then the case 36 is not required.

The features shown in FIGS. 3 to 4B may be summarised as follows:

FIG. 3

18 Electrodeless bulb with a mercury-based bulb fill for a maximum output in the 200 to 260 nm germicidal UV spectral range.

24 Strengthened quartz end to bulb for mounting purposes and also to allow UV from igniter bulb to enter bulb.

26 Face of shaft 2 to permit UV entry.

30 Separate quartz piece may be used to conduct UV energy to main bulb from igniter bulb.

FIGS. 4A and 4B

32 Electrodeless bulb-holder.

18 Mercury-based fill in electrodeless bulb for producing UV energy in the germicidal spectrum of 200 to 260 nm.

6 Article to be sterilised.

36 Outer case which is substantially transparent to microwave energy but substantially opaque to UV energy.

34 Clips to mount article so that no internal contact is made with UV-producing bulb but so that UV can reach all internal areas to be sterilised.

38 Outer case and designed such that unless closed, case does not fit in microwave enclosure (to prevent UV leakage).

Figure 5:
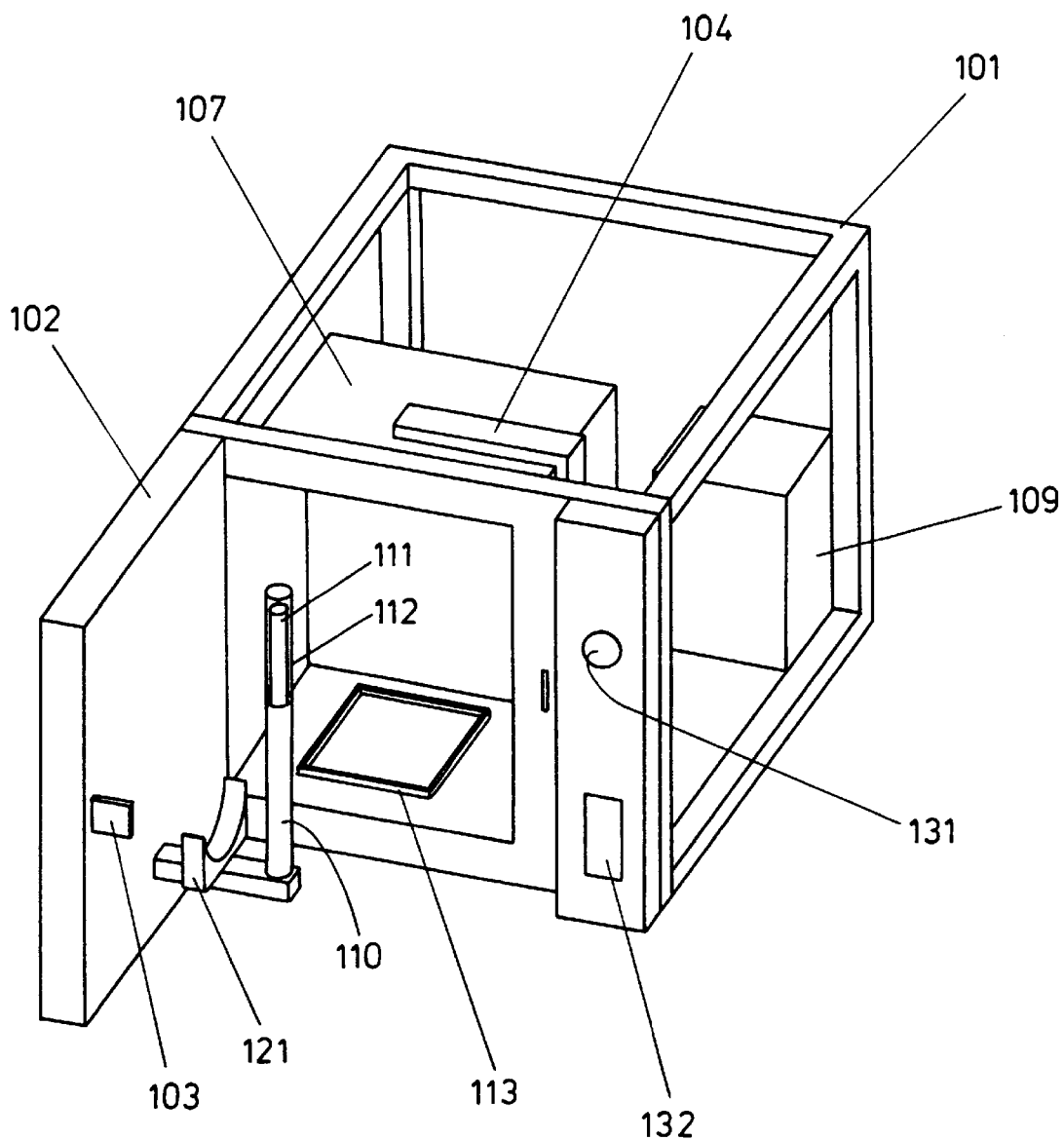
FIG. 5 shows a schematic perspective view of a further embodiment.

In the embodiment shown in FIG. 5, the sterilisation unit comprises a main housing 101 having a side hinged door 102, said door having interlocking means 103 to enable the actuation of the sterilising unit. The interlocking means are disengageable by means of a control button 131. The door 102 forms the opening of a chamber 107, which chamber is situated within the main housing 101. Further disposed on the main housing is a control panel 132, enabling the correct dose to be selected for the container to be sterilised and for the sterilising process to be actuated. Within the main housing there is provided a magnetron 104 which together with control electronics 105 and power supply 106 acts as a microwave generator, which, in this embodiment, generates microwaves with a frequency of 2.45 GHz. The unit is constructed such as to ensure compliance with health and safety regulations, such as EC directive 82/499. To enable the magnetron to operate using mains electricity, a transformer 109 is provided. The microwaves thus generated are then directed through a plastic window into the chamber 107. A support member 120 extends horizontally from the inner face of the door 102 and supports, at its outer end, an upstanding hollow column 110.

The support member 120 is dimensioned such that when the door is closed the hollow column is located generally in the centre of the chamber. Situated inside the column 110 is a sealed unit 111, such as a quartz tube, which sealed unit contains a gas or plasma capable of emitting ultraviolet light with a frequency suitable for sterilisation, for example mercury vapour. The hollow column 110 forms a shield to protect the bulb and has additionally an air passage 112 around the sealed unit. Compressed air or gas is supplied to the lower end of the column by means of a compressor and filter (not shown) via suitable tubing, such as a plastic material or rubber. The air or gas is then passed into the air passage 112, whence it rises to the upper end of the column exiting through holes 122, thereby having a cooling effect on the sealed unit, which otherwise could reach temperatures sufficient to cause deformation to a plastic container placed over the sealed unit and hollow column 110. The column 110 is adapted to be robust enough to prevent damage to the sealed unit from the action of placing the container over it.

By mounting the column 110 on the door, the column is fully exposed when the door 102 is open, thereby facilitating the placement of the container to be sterilised and permitting a reduction in size of the chamber. The support member 120 also incorporates holding means 121, adapted to hold a cap or lid for the container.

Disposed on the base of the chamber 107 and located substantially underneath the hollow column 110 when the door is closed is a drip tray 113 adapted to retain any water or particles of debris or other material removed from the container, for example by the action of the compressed air.

Figure 6:
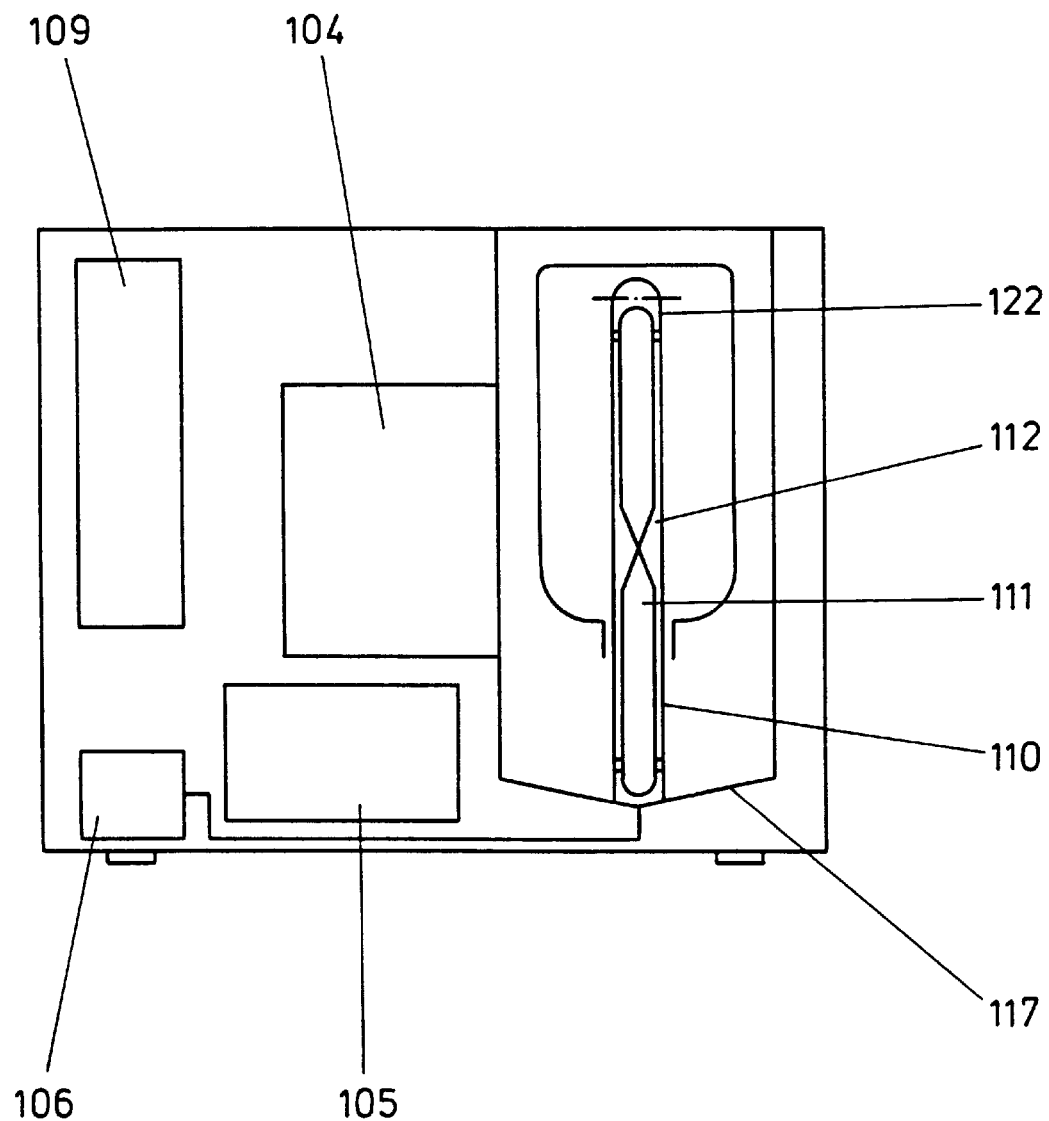
FIG. 6 shows a schematic side view of another embodiment comprising a container dryer and steriliser apparatus adapted to be located on a worktop.

In a further embodiment, shown in FIG. 6, the sterilisation unit includes a magnetron as described with reference to the first embodiment and a microwave cavity 117, which cavity is situated within the main housing 101. The microwave cavity is principally constructed of metal and is further provided with a plastic window, which is transparent to microwaves.

In this embodiment the hollow column 110 is constructed of a plastic material, such as PTFE, transparent to microwaves and ultraviolet light in the range from 200 nm to 400 nm, which wavelengths are known to have germicidal properties. At the upper end of the hollow column are a plurality of holes adapted to release the air or gas supplied to the hollow column.

Figure 7:
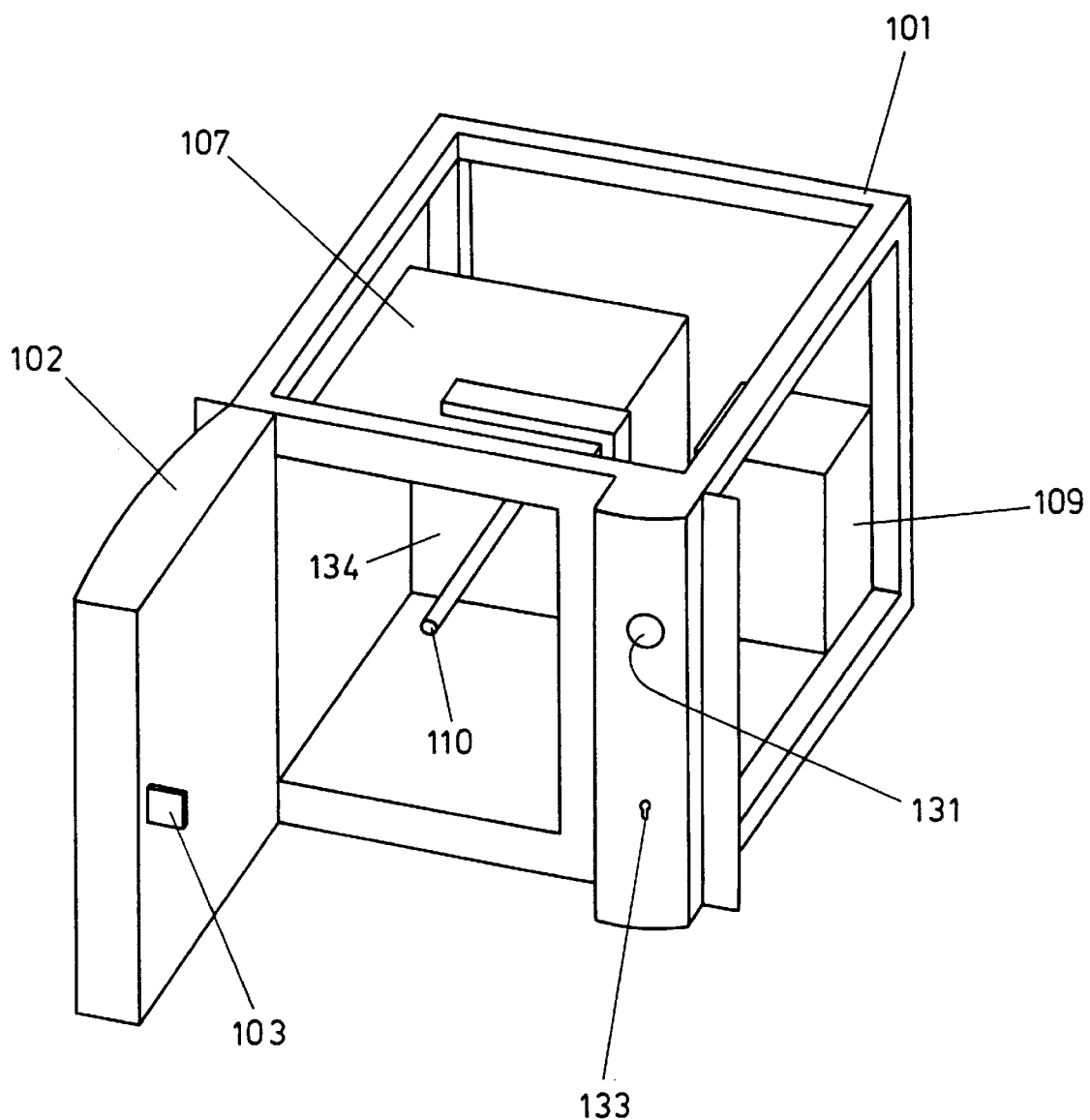
FIG. 7 shows an embodiment with an alternative mounting position for the elongate member.

FIG. 7 illustrates a modified form of the apparatus shown in FIG. 5, in which like parts bear like references. In this embodiment, the column 110 is mounted so as to extend horizontally from a back wall 134 of the chamber. This arrangement has the advantage that, since the column 110 is mounted close to the magnetron 104, the electrical circuitry is more compact and simplified which reduces cost and simplifies manufacture.

It is also envisaged that the hollow column may be of an open frame or lattice type structure, that is having a plurality of openings located along its length. This embodiment could enable the hollow column 110 to be constructed of a material not transparent to microwaves.

Additionally the source of ultraviolet light could be any common source such as a electrically actuated mercury vapour discharge lamp.

It is further envisaged that the hollow column could be adapted to incorporate a microwave emitter or waveguide, thereby enabling both embodiments to be adapted for use with containers which are not transparent to microwaves.

In operation a container, which in both embodiments must be at least partially transparent to microwaves, is placed upside down onto the hollow column 110 (FIGS. 5 and 6), or horizontally on the column (FIG. 7). The container size is then entered by means of the control panel and the sterilisation process actuated, in which air is then passed up the hollow column into the container thereby removing any water or loose particles. Simultaneously the cavity is irradiated with microwaves which pass through the container and the wall of the hollow column into the sealed unit 111, the microwaves thereby exciting the gas or plasma, causing it to emit ultraviolet light having a wavelength between 200 nm and 400 nm. The ultraviolet light thus emitted irradiates the inner surface of the container thereby rendering the container sterile. The cycle time is of the order of a few seconds.

We claim:

1. A sterilizing apparatus for sterilizing a container, the apparatus comprising:

an elongate member adapted to emit ultra violet light having sterilizing properties when energized;

microwave generator adapted to generate microwaves, said elongate member being irradiated to emit said ultra violet light when energized by said microwaves; and a shield substantially surrounding, and spacially removed from, said elongate member and being adapted to shield said elongate member from physical damage, wherein, in order to sterilize the interior of a container, the elongate member is located substantially entirely within the container and energized.

2. The apparatus according to claim 1, wherein the elongate member and the surrounding shield are disposed in an upstanding manner in a chamber.

3. The apparatus according to claim 1, wherein the elongate member and the surrounding shield are mounted on a side wall of said chamber.

4. The apparatus according to claim 3, wherein said side wall is opposite a side of said chamber containing a door.

5. The apparatus according to claim 1, wherein the chamber incorporates a hinged door, the elongate member and the shield being mounted on an inner surface of said door so that when the door is opened the elongate member and shield are clearly exposed to facilitate the placement of a container over the shield.

6. The apparatus according to claim 5, including switch means adapted to be triggered by closing the door to thereby close a contact which then initiates irradiation of the ultra violet light source.

7. The apparatus according to claim 1, further comprising control means to enable the length of time that the elongate member is irradiated to be adjustable.

8. The apparatus according to claim 1, wherein the shield comprises a closed tube formed of a plastics material which is substantially transparent to ultra violet light and microwaves.

9. The apparatus according to claim 1 which further includes supply means to supply air or a gas to the interior of the shield to cool the elongate member when it is emitting ultra violet light.

10. The apparatus according to claim 9, wherein the tube incorporates orifices towards an end, located opposite said supply means, so that the supplied air leaves the tube and enters the interior of the container being sterilized.

11. The apparatus according to claim 1, wherein the tube comprises an open frame work or lattice work.

12. The apparatus according to claim 11, wherein the openings in the shield are sufficient to allow the microwaves to penetrate to irradiate the elongate member.

13. The apparatus according to claim 1, wherein the shield forms, at least in part, a wave guide for microwaves generated by a magnetron.

14. The apparatus according to claim 13, wherein the chamber has an outlet vent incorporating a mist eliminator to trap particles of water and vapor contained in the air being vented from the chamber.

15. The apparatus according to claim 14, wherein the mist eliminator comprises a wire mesh.

16. The apparatus according to claim 14, further including a drip tray for moisture driven out of the container and/or the mist eliminator.

17. The apparatus according to claim 1, further including a support for the shield and elongate member, the support being adapted to be removably placeable in a chamber of a microwave oven.

18. The apparatus according to claim 17, wherein the support is located in a casing adapted to be removably placeable in a chamber of a microwave oven.

19. The apparatus according to claim 1, further comprising means for suspending the elongate member inside the container.

* * * * *